United States Patent [19]

Alker et al.

[11] Patent Number: 4,618,609
[45] Date of Patent: Oct. 21, 1986

[54] ANTI-ISCHAEMIC AND ANTIHYPERTENSIVE 2-[PYRIMIDYLOXY ALHOXYMETHYL]-1,4-DIHYDROPYRIDINES

[75] Inventors: David Alker, Eastry; Simon F. Campbell, Deal; Peter E. Cross, Canterbury, all of England

[73] Assignee: Pfizer Inc., New York, N.Y.

[21] Appl. No.: 741,339

[22] Filed: Jun. 5, 1985

[30] Foreign Application Priority Data

Jun. 7, 1984 [GB] United Kingdom ................ 8414520
Apr. 3, 1985 [GB] United Kingdom ................ 8508736

[51] Int. Cl.$^4$ ................ C07D 401/12; C07D 413/14; C07D 401/14; A61K 31/505
[52] U.S. Cl. ................ 514/236; 514/252; 544/310; 544/316; 544/317; 544/319; 544/321; 544/122; 544/123
[58] Field of Search ............ 544/316, 317, 310, 321, 544/319, 122, 123; 514/252, 236

[56] References Cited

U.S. PATENT DOCUMENTS 4,515,799  5/1985  Campbell .................... 544/333
4,572,908  2/1986  Campbell .................... 544/333

Primary Examiner—Henry R. Jiles
Assistant Examiner—Dale A. Bjorkman
Attorney, Agent, or Firm—Charles J. Knuth; Albert E. Frost; James M. McManus

[57] ABSTRACT

Dihydropyridine derivatives of the formula:

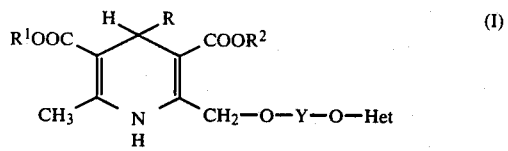

and their pharmaceutically acceptable acid addition salts; wherein
R is a substituted aryl group;
$R^1$ and $R^2$ are each independently $C_1$-$C_3$ alkyl;
Y is —$(CH_2)_n$— where n is 2, or —$CH_2CH(CH_3)$—;
and Het is a 6-membered aromatic heterocyclic group attached to the adjacent oxygen atom by a carbon atom.

The compounds have utility as anti-ischaemic and antihypertensive agents.

11 Claims, No Drawings

ANTI-ISCHAEMIC AND ANTIHYPERTENSIVE 2-[PYRIMIDYLOXY ALHOXYMETHYL]-1,4-DIHYDROPYRIDINES

BACKGROUND OF THE INVENTION

This invention relates to certain dihydropyridines, specifically to certain 1,4-dihydropyridines having a heterocyclic group in a side chain attached to the 2-position, which have utility as anti-ischaemic and antihypertensive agents.

The compounds of the invention reduce the movement of calcium into the cell and they are thus able to delay or prevent the cardiac contracture which is believed to be caused by an accumulation of intracellular calcium under ischaemic conditions. Excessive calcium influx during ischaemia can have a number of additional adverse effects which would further compromise the ischaemic myocardium. These include less efficient use of oxygen for ATP production, activation of mitochondrial fatty acid oxidation and possibly, promotion of cell necrosis. Thus the compounds are useful in the treatment or prevention of a variety of cardiac conditions, such as angina pectoris, cardiac arrhythmias, heart attacks and cardiac hypertrophy. The compounds also have vasodilator activity since they can inhibit calcium influx in cells of vascular tissue and they are thus also useful as antihypertensive agents and for the treatment of coronary vasopasm.

SUMMARY OF THE INVENTION

Thus according to the invention there are provided dihydropyridines of the formula:

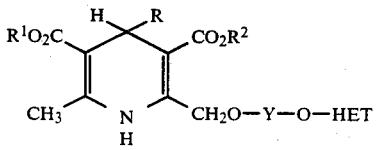

and their pharmaceutically acceptable acid addition salts, where R is 2-chlorophenyl or 2,3-dichlorophenyl; $R^1$ and $R^2$ are each alkyl of one to three carbon atoms; Y is —(CH$_2$)$_2$— or —CH$_2$CH(CH$_3$)—; and HET is 2- or 4-pyrimidyl or substituted 2- or 4-pyrimidyl where the substituent is carbamoyl, amino, alkoxy of one to three carbon atoms, chloro, 2-aminoethylamino, 2-hydroxyethylamino, 2-pyridylmethylamino, 2,3-dihydroxypropylamino, 2-pyridylmethoxy, 1-methyl-2-imidazolylmethoxy or morpholino.

A preferred series of compounds are those wherein $R^1$ is methyl, $R^2$ is ethyl and Y is —(CH$_2$)$_2$—. Especially preferred within this series are the compounds wherein R is 2-chlorophenyl and 2,3-dichlorophenyl and HET is 2-pyrimidyl or 4-pyrimidyl.

Also preferred are compounds wherein $R^1$ is methyl, $R^2$ is ethyl, Y is —(CH$_2$)$_2$— and HET is substituted 4-pyrimidyl wherein the substituent is carbamoyl, amino, alkoxy of one to three carbon atoms, chloro, 2-aminoethylamino, 2-hydroxyethylamino, 2-pyridylmethylamino, 2,3-dihydroxypropylamino, 2-pyridylmethoxy, 1-methyl-2-imidazolylmethoxy or morpholino. Especially preferred within this group are the compounds wherein R is 2-chlorophenyl or 2,3-dichlorophenyl.

The present invention also relates to a pharmaceutical composition of the instant compounds and a pharmaceutically acceptable carrier and a method of treating hypertension in a mammal by treatment with an effective antihypertensive amount of a compound of the present invention.

The pharmaceutically acceptable acid addition salts of the compounds of the formula (I) are those formed from acids which form non-toxic acid addition salts, for example the hydrochloride, hydrobromide, sulphate or bisulphate, phosphate or acid phosphate, acetate, citrate, fumarate, gluconate, lactate, maleate, succinate, mesylate and tartrate salts.

DETAILED DESCRIPTION OF THE INVENTION

The compounds of the invention can be prepared by a number of routes, including the following:

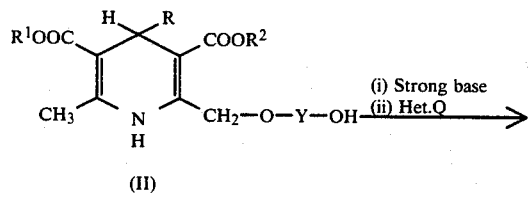

The compounds of the formula (I).

Q is a leaving group such as Cl, Br, I, —NH.NO$_2$ or $C_1$-$C_4$ alkylthio.

Q is preferably Cl. $R^1$, $R^2$, Y and Het are as defined for formula (I).

The reaction is typically carried out by adding a strong base such as sodium hydride or potassium t-butoxide to a solution of the dihydropyridine (II) in a suitable organic solvent, e.g. tetrahydrofuran, followed by stirring for a short period so as to form a base salt, e.g. th sodium or potassium salt, of the compound (II). The compound Het.Q is then added and the resulting solution is then stirred, typically at room temperature, until the reaction is complete. If desired, the reaction mixture can be heated at up to 100° C. to speed up the rate of reaction. The product (I) can then be isolated and purified conventionally.

The intermediate dihydropyridines of the formula (II) can be prepared as follows:

(a) Intermediates in which Y is —(CH$_2$)$_2$— can be prepared as follows:

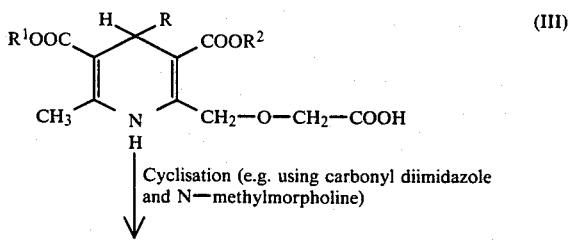

-continued

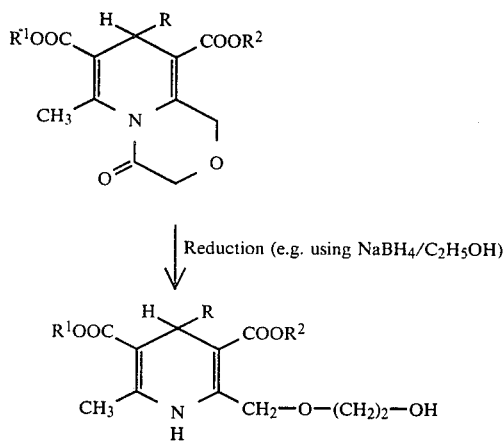

The cyclisation is typically carried out by stirring the dihydropyridine (III), carbonyl diimidazole and N-methylmorpholine in a suitable organic solvent, e.g. tetrahydrofuran, until the reaction is complete. The product (IV) can then be recovered by conventional means. The reduction can then be carried out by reducing the oxazinone (IV) with sodium borohydride in ethanol at room temperature. The product can again be isolated and purified conventionally.

The starting materials of the formula (III) are either known compounds or can be prepared analogously to the prior art, see e.g. European patent application publication No. 0100189. A typical procedure is as follows:

(a)

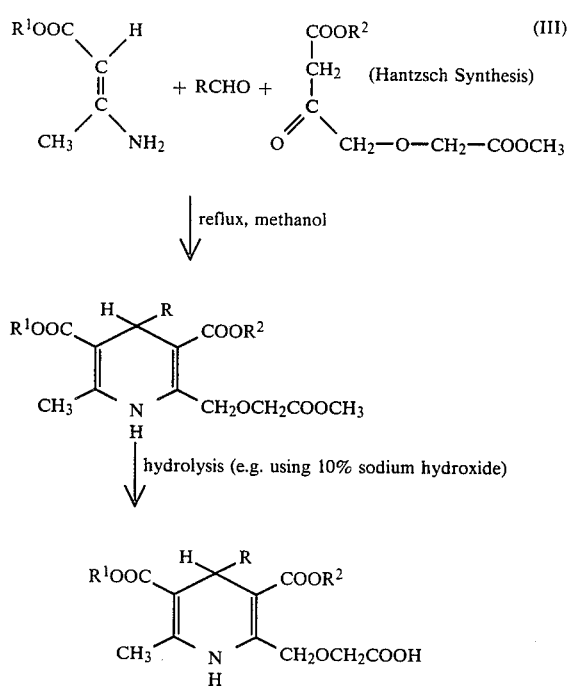

(b) Intermediates in which Y is —CH$_2$CH(CH$_3$)— can be prepared as follows:

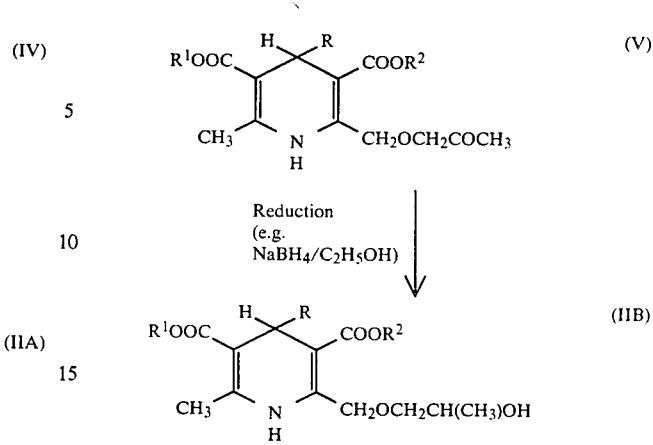

The reduction is typically carried out by reducing the ketone (V) with e.g. sodium borohydride in a suitable organic solvent, e.g. ethanol, at room temperature. The product (IIB) can then be isolated conventionally.

The ketones (V) can be prepared from the acids (III). This method typically involves the reaction of the acid (III) with carbonyldiimidazole, e.g. in dichloromethane, to form the imidazolide. Reaction of this with 2,2-dimethyl-1,3-dioxane-4,6-dione in the presence of pyridine and in e.g. dichloromethane, followed by hydrolysis using e.g. aqueous acetic acid under reflux, yields the ketone (V).

Alternatively the ketones (V) can be prepared by hydrolysis of acetylenes of formula (VII) using mercuric ions (e.g. derived from mercuric sulphate) with aqueous mineral acid (e.g. H$_2$SO$_4$ in aqueous dioxane). Typically the reaction is carried out with a moderate degree of heating e.g. 50°–70° C.

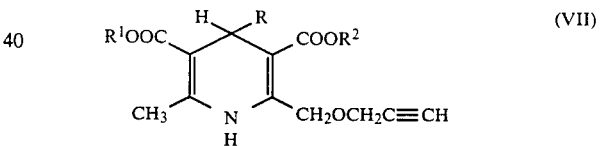

The acetylenes (VII) are available by a standard Hantzsch synthesis.

(c) Intermediates in which Y is —(CH$_2$)$_n$— where n is 2,3 or 4 can be prepared by the reduction of the appropriate acid of the formula:

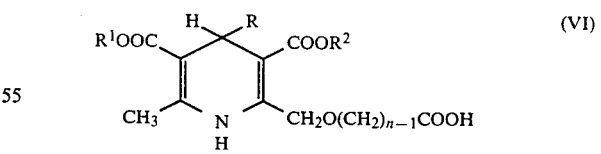

The preferred reducing agent is borane, and the reaction is typically carried out in tetrahydrofuran.

The starting materials (VI) can be prepared by the Hantzsch synthesis [see route (a)] using the appropriately 4-substituted acetoacetate, followed by hydrolysis of the resulting ester using e.g. 10% sodium hydroxide.

(2) Compounds in which Het is a heterocyclic group substituted by an amino, substituted amino group or cyclic amino group, e.g. morpholino, piperidino or 4-methylpiperazin-1-yl, can be prepared by heating the corresponding chloro-, bromo- or iodo-substituted compounds with the appropriate amine.

Compounds in which Het is a heterocyclic group substituted by (2-aminoethyl)amino can be prepared by the reaction of the corresponding halo-substituted (preferably chloro-substituted) compound with 1,2-diaminoethane. and (3) Acid addition salts (where the compounds form such salts) can be prepared conventionally, e.g. by reacting a solution of the free base in a suitable organic solvent with a solution of the desired acid in a suitable solvent, and either recovering the salt by filtration when it precipitates from solution, or by evaporation of the solution to dryness.

The ability of the compounds to inhibit the movement of calcium into the cell is shown by their effectiveness in reducing the contraction of vascular tissue in vitro which is the consequence of calcium influx caused by a high extracellular concentration of potassium ions. The test is performed by mounting spirally cut strips of rat aorta with one end fixed and the other attached to a force transducer. The tissue is immersed in a bath of physiological saline solution containing 2.5 mM $Ca^{2+}$ and 5.9 mM $K^{\oplus}$. Potassium chloride solution is added to the bath with a pipette to give a final $K^{\oplus}$ concentration of 45 millimolar. The change in tension caused by the resulting contraction of the tissue is noted. The bath is drained and refilled with fresh saline solution and, after 45 minutes, the test is repeated with the particular compound under test present in the saline solution. The concentration of compound required to reduce the response by 50% ($IC_{50}$) is recorded.

The antihypertensive activity of the compounds is evaluated after oral administration by measuring the fall in blood pressure in spontaneously hypertensive rats or renally hypertensive dogs.

For administration to man in the curative or prophylactic treatment of cardiac conditions and hypertension, oral dosages of the compounds will be in the range of from 5-100 mg daily for an average adult patient (70 kg), typically 10-60 mg daily. Thus for a typical adult patient, individual tablets or capsules will generally contain 5, 10 or 20 mg of active compound, in a suitable pharmaceutically acceptable vehicle or carrier. Dosages for intravenous administration will typically be within the range 1 to 10 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic.

Thus in a further aspect the invention provides a pharmaceutical composition comprising a compound of the formula (I), or a pharmaceutically acceptable salt thereof, together with a pharmaceutically acceptable diluent or carrier.

The invention also includes a compound of the formula (I), or a pharmaceutically acceptable salt thereof, for use in medicine, in particular for use in the treatment of ischaemic heart disease, angina, or hypertension in a human being.

The invention also provides a method of protecting the heart from the deleterious effects of ischaemia, which comprises administering an effective amount of a compound of the formula (I) or pharmaceutically acceptable salt thereof, or a pharmaceutical composition as defined above.

The invention also includes a method of treating hypertension which comprises administering an antihypertensive amount of a compound of the formula (I) or pharmaceutically acceptable salt thereof, or pharmaceutical composition as defined above.

The following Examples, in which all temperatures are in °C., illustrate the invention:

EXAMPLE 1

4-(2-Chlorophenyl)-3-ethoxycarbonyl-5-methoxycarbonyl-6-methyl-2-[2-(2-pyrimidinyloxy)ethoxymethyl]-1,4-dihydropyridine Sodium hydride (90 mg of an 80% by weight dispersion in oil) was added to a solution of 4-(2-chlorophenyl)-3-ethoxycarbonyl-2-(2-hydroxyethoxymethyl)-5-methoxycarbonyl-6-methyl-1,4-dihydropyridine (0.60 g) in tetrahydrofuran (20 ml) and the mixture stirred at room temperature for 45 minutes and then treated with 2-chloropyrimidine (0.17 g). The mixture was stirred at room temperature for 3 days and evaporated. The residue was dissolved in ethyl acetate and the solution washed successively with 2M hydrochloric acid, 5% aqueous sodium carbonate solution and brine, dried over $MgSO_4$ and evaporated. The residue was crystallised from ether to give the title compound (90 mg), m.p. 101°.

Analysis %: Found: C,58.77; H,5.52; N,8.50. $C_{24}H_{26}ClN_3O_6$ requires: C,59.07; H,5.37; N,8.61.

EXAMPLES 2-8

The following compounds were prepared using appropriate starting materials by the method described in Example 1.

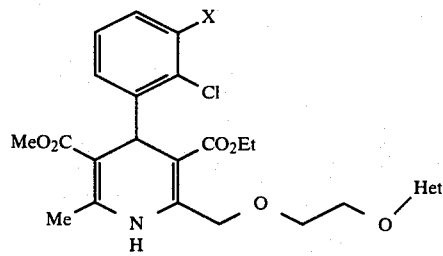

| Example No. | X | Het | m.p. (°C.) | Analysis % (Theoretical in Brackets) or n.m.r. | | |
|---|---|---|---|---|---|---|
| | | | | C | H | N |
| 2 | H | (pyrimidinyl with CONH₂) | 160–161 | 56.55 (56.55 | 5.22 5.13 | 10.54 10.55) |
| 3 | H | (pyrimidinyl with NH₂) | 168–171 | 57.26 (57.31 | 5.67 5.41 | 10.54 11.14) |
| 4 | H | (pyrimidinyl with Cl) | oil | N.m.r. (CDCl₃).δ = 8.63 (1H, s); 6.9–7.5 (5H, m); 6.84 (2H, s); 5.41 (1H, s); 4.80 (2H, s); 4.55–4.8 (2H, m); 4.08 (2H, q, J = 7 Hz); 3.8–4.1 (2H, m); 3.62 (3H, s); 2.33 (3H, s) and 1.19 (3H, t, J = 7 Hz). | | |
| 5 | H | (pyrimidinyl with OMe) | 102–104 | 58.20 (57.97 | 5.50 5.45 | 7.91 8.11) |
| 6 | Cl | (pyrimidinyl) | 148–149* | 54.33 (54.24 | 4.72 4.89 | 8.08 7.90) |
| 7 | Cl | (pyrimidinyl with OMe) | 95–97 | 54.19 (54.25 | 4.93 4.88 | 7.09 7.60) |
| 8 | Cl | (pyrimidinyl with Cl) | 76–78 | 52.04 (51.75 | 4.56 4.31 | 7.30 7.55) |

*Characterised as the hemihydrate.

EXAMPLE 9

6-(2-aminoethyl)amino-4-<2-{[4-(2-chlorophenyl)-3-ethoxycarbonyl-5-methoxycarbonyl-6-methyl-1,4-dihydropyrid-2-yl]methoxy}ethoxy>pyrimidine A mixture of 6-chloro-4-<2-{[4-(2-chlorophenyl)-3-ethoxycarbonyl-5-methoxycarbonyl-6-methyl-1,4-dihydropyrid-2-yl]methoxy}ethoxy>pyrimidine (0.52 g) and 1,2-diaminoethane (5 ml) was stirred at room temperature for 17 hours and then partitioned between ethyl acetate and water. The organic layer was washed twice with water, dried over Na₂SO₄ and evaporated. The residue was triturated with ether and the resulting solid was collected, washed with ether and dried to give the title compound as its hemihydrate (0.15 g), m.p. 79°–82°.

Analysis %: Found: C,56.63; H,5.85; N,12.42. C₂₆H₃₂Cl₂N₅O₆.0.5 H₂O requires: C,56.26; H,5.99; N,12.62.

EXAMPLE 10

4-<2-{[4-(2,3-Dichlorophenyl)-3-ethoxycarbonyl-5-methoxycarbonyl-6-methyl-1,4-dihydropyrid-2-yl]methoxy}ethoxy>-6-(2-hydroxyethylamino)pyrimidine A mixture of 6-chloro-4-<2-{[4-(2,3-dichlorophenyl)-3-ethoxycarbonyl-5-methoxycarbonyl-6-methyl-1,4-dihydropyrid-2-yl]methoxy}ethoxy>pyrimidine (1.00 g) and ethanolamine (10 ml) was heated at 90° C. for 4 hours and then partitioned between dichloromethane and water. The organic layer was washed successively with 2M hydrochloric acid, water, 10% aqueous sodium carbonate solution and water, dried over Na₂SO₄ and evaporated. The residue was purified by chromatography on silica (8 g) using dichloromethane plus 50% v/v hexane followed by dichloromethane plus 0–1% v/v methanol as eluant. Appropriate fractions were combined and evaporated and the residue recrystallised from ether to give the title compound (269 mg), m.p. 114°–115° C.

Analysis %: Found: C,53.43; H,5.74; N,9.93. C₂₆H₃₀Cl₂N₄O₇ requires: C,53.70; H,5.16; N,9.63.

EXAMPLE 11

4-<2-{[4-(2,3-Dichlorophenyl)-3-ethoxycarbonyl-5-methoxycarbonyl-6-methyl-1,4-dihydropyrid-2-yl]methoxy}ethoxy>-6-(2-pyridylmethylamino)pyrimidine was prepared by the method described in Example 10 using 2-aminomethylpyridine instead of ethanolamine as the starting material. The product had m.p. 115°–116° C.

Analysis %: Found: C,57.45; H,4.98; N,10.90. C₃₀H₃₁Cl₂N₅O₆ requires: C,57.32; H,4.93; N,11.15.

EXAMPLE 12

4-<2-{[4-(2,3-Dichlorophenyl)-3-ethoxycarbonyl-5-methoxycarbonyl-6-methyl-1,4-dihydropyrid-2-yl]methoxy}ethoxy>-6-(2,3-dihydroxypropylamino)pyrimidine was prepared by the method described in Example 10 using 1-amino-2,3-dihydroxypropane instead of ethanolamine as the starting material. The product was characterized as its hemihydrate, m.p. 112°–114° C.

Analysis %: Found: C,52.47; H,5.30; N,9.10. C₂₇H₃₂Cl₂N₄O₈.0.5 H₂O requires: C,52.25; H,5.32; N,9.03.

EXAMPLE 13

4-<2-{[4-(2,3-Dichlorophenyl)-3-ethoxycarbonyl-5-methoxycarbonyl-6-methyl-1,4-dihydropyrid-2-yl]methoxy}ethoxy>-6-(2-pyridylmethoxy)pyrimidine Sodium hydride (0.12 g of an 80% by weight dispersion in oil) was added to a solution of 4-(2,3-dichlorophenyl)-3-ethoxycarbonyl-2-(2-hydroxyethoxymethyl)-5-methoxycarbonyl-6-methyl-1,4-dihydropyridine (0.90 g) in tetrahydrofuran (30 ml) and the mixture stirred at room temperature for one hour. A solution of 4-chloro-6-(2-pyridylmethoxy)pyrimidine (0.44 g) in tetrahydrofuran (10 ml) was added to the reaction mixture which was then stirred at room temperature for 16 hours, quenched into water and extracted into dichloromethane. The organic layer was dried over Na₂SO₄ and evaporated. The residue was purified by chromatography on silica (10 g) using dichloromethane plus 50% v/v hexane followed by dichloromethane plus 0–5% v/v methanol as eluant. Appropriate fractions were combined and evaporated and the residue crystallised from ether to give the title compound (0.23 g), m.p. 95°–96° C.

Analysis %: Found: C,57.01; H,4.77; N,8.60. C$_{30}$H$_{30}$Cl$_2$N$_4$O$_7$ requires: C,57.41; H,4.46; N,8.93.

EXAMPLE 14

4-<2-{[4-(2-Chlorophenyl)-3-ethoxycarbonyl-5-methoxycarbonyl-6-methyl-1,4-dihydropyrid-2-yl]methoxy}ethoxy>-6-(2-pyridylmethoxy)pyrimidine was prepared by the method described in Example 13 using 4-(2-chlorophenyl)-3-ethoxycarbonyl-2-(2-hydroxyethoxymethyl)-5-methoxycarbonyl-6-methyl-1,4-dihydropyridine and 4-chloro-6-(2-pyridylmethoxy)pyrimidine as the starting materials. The product had m.p. 64°–67° C.

'H-n.m.r. (CDCl$_3$, δ): 8.63 (1H, d, J=6 Hz), 8.47 (1H, s), 7.05–7.80 (7H, m), 6.22 (1H, s), 5.55 (2H, s), 5.41 (1H, s), 4.81 (2H, s), 4.60–4.85 (2H, m), 4.09 (2H, q, J=7 Hz), 3.80–4.10 (2H, m), 3.62 (3H, s), 2.32 (3H, s) and 1.20 (3H, t, J=7 Hz).

EXAMPLE 15

4-<2-{[4-(2-Chlorophenyl)-3-ethoxycarbonyl-5-methoxycarbonyl-6-methyl-1,4-dihydropyrid-2-yl]methoxy}ethoxy>-6-(1-methyl-2-imidazolylmethoxy)-pyrimidine was prepared by the method described in Example 13 using 4-chloro-6-(1-methyl-2-imidazolylmethoxy)pyrimidine and 4-(2-chlorophenyl)-3-ethoxycarbonyl-2-(2-hydroxyethoxymethyl)-5-methoxycarbonyl-6-methyl-1,4-dihydropyridine as the starting materials. The product had m.p. 48°–51° C.

Analysis %: Found: C,54.59; H,5.03; N, 10.76. C$_{29}$H$_{31}$Cl$_2$N$_5$O$_7$ requires: C,54.29; H,4.99; N,10.92.

EXAMPLE 16

4-<2-{[4-(2,3-Dichlorophenyl)-3-ethoxycarbonyl-5-methoxycarbonyl-6-methyl-1,4-dihydropyrid-2-yl]methoxy}ethoxy>-6-morpholinopyrimidine. A mixture of 6-chloro-4-<2-{[4-(2,3-dichlorophenyl)-3-ethoxycarbonyl-5-methoxycarbonyl-6-methyl-1,4-dihydropyrid-2-yl]methoxy}ethoxy>pyrimidine (0.50 g) and morpholine (10 ml) was stirred at room temperature for 17 hours and then partitioned between ethyl acetate and water. The organic layer was washed twice with water, dried over Na$_2$SO$_4$ and evaporated. The residue was triturated with ether and the resulting solid was collected, washed with ether and dried to give the title compound (67 mg), m.p. 120°–121° C.

Analysis %: Found: C,55.04; H,5.31; N,8.84. C$_{28}$H$_{32}$Cl$_2$N$_4$O$_7$ requires: C,55.35; H,5.47; N,9.22.

The following Preparations illustrate the preparation of certain starting materials. All temperatures are in °C.:

PREPARATION 1

4-(2-Chlorophenyl)-3-ethoxycarbonyl-2-(2-hydroxyethoxymethyl)-5-methoxycarbonyl-6-methyl-1,4-dihydropyridine A 1M solution of borane in tetrahydrofuran (10 ml) was added dropwise over 10 minutes to a stirred, ice-cooled solution of 2-{[4-(2-chlorophenyl)-3-ethoxycarbonyl-5-methoxycarbonyl-6-methyl-1,4-dihydropyrid-2-yl]methoxy}acetic acid (2.0 g—see preparation 4 of European patent application publication No. 0100189) in tetrahydrofuran (20 ml) and the mixture was allowed to warm to room temperature. The mixture was stirred at room temperature for 3 days, quenched with water (5 ml) and evaporated. The residue was partitioned between ethyl acetate and saturated aqueous sodium hydrogen carbonate solution and the organic layer was dried over MgSO$_4$ and evaporated. The residual oil was purified by chromatography on silica gel (10 g) using hexane plus 20→50% dichloromethane followed by dichloromethane plus 0→1% methanol as eluant. Appropriate fractions were combined and evaporated and the resulting oil was crystallised from hexane to give the title compound (0.6 g), m.p. 125°–130°.

'H-n.m.r. (CDCl$_3$, δ): 7.0–7.65 (5H, m); 5.48 (1H, s); 4.81 (2H, s); 4.12 (2H, q, J=7 Hz); 3.5–4.0 (4H, m); 3.65 (3H, s); 2.38 (3H, s) and 1.21 (3H, t, J=7 Hz).

PREPARATION 2

4-(2,3-Dichlorophenyl)-3-ethoxycarbonyl-2-(2-hydroxyethoxymethyl)-5-methoxycarbonyl-6-methyl-1,4-dihydropyridine was prepared by the method described in Preparation 1 using 2-{[4-(2,3-dichlorophenyl)-3-ethoxycarbonyl-5-methoxycarbonyl-6-methyl-1,4-dihydropyrid-2-yl]methoxy}acetic acid (see Preparation 5 of European patent application publication No. 0100189) and borane as the starting materials. The product had a m.p. of 120°–121°.

Analysis %: Found: C,54.30; H,5.49; N,3.13. C$_{20}$H$_{23}$Cl$_2$NO$_6$ requires: C,54.06; H,5.22; N,3.15.

PREPARATION 3

(A)

7-(2,3-Dichlorophenyl)-8-ethoxycarbonyl-6-methoxycarbonyl-5-methyl-3-oxo-2,3,7,9-tetrahydropyrido[1,2-c]-1,4-oxazine A solution of 2-{[4-(2,3-dichlorophenyl)-3-ethoxycarbonyl-5-methoxycarbonyl-6-methyl-1,4-dihydropyrid-2-yl]methoxy}acetic acid (9.16 g), carbonyl diimidazole (3.60 g) and M-methylmorpholine (3.5 ml) in tetrahydrofuran (30 ml) was stirred at room temperature for 16 hours and then evaporated. The residue was taken up in dichloromethane and the solution washed with 2M hydrochloric acid, 10% aqueous sodium carbonate solution and water, dried over Na$_2$SO$_4$ and evaporated. Recrystallisation of the residue from ethyl acetate gave the title compound (4.70 g), m.p. 172°–173°.

Analysis %: Found: C,53.27; H,4.27; N,3.15. C$_{20}$H$_{19}$Cl$_2$NO$_6$ requires: C,53.27; H,4.44; N,3.27.

(B)

4-(2,3-Dichlorophenyl)-3-ethoxycarbonyl-2-(2-hydroxyethoxymethyl)-5-methoxycarbonyl-6-methyl-1,4-dihydropyridine A mixture of sodium borohydride (1.52 g) and 7-(2,3-dichlorophenyl)-8-ethoxycarbonyl-6-methoxycarbonyl-5-methyl-3-oxo-2,3,7,9-tetrahydropyrido[1,2-c]-1,4-oxazine (9.00 g) in ethanol (100 ml) was stirred at room temperature for 16 hours and then evaporated. The residue was taken up in dichloromethane and the solution was washed with water, 2M hydrochloric acid and water, dried over Na$_2$SO$_4$ and evaporated. The residue was crystallised from ether to give the title compound (6.00 g), m.p. 120°–121°. This material was confirmed spectroscopically to be identical with that obtained by the procedure of Preparation 2.

PREPARATION 4

(A)

1-{[4-(2,3-Dichlorophenyl)-3-ethoxycarbonyl-5-methoxycarbonyl-6-methyl-1,4-dihydropyrid-2-yl]methoxy}acetone A solution of carbonyl diimidazole (8.00 g) and 2-{[4-(2,3-dichlorophenyl)-3-ethoxycarbonyl-5-methoxycarbonyl-6-methyl-1,4-dihydropyrid-2-yl]methoxy}acetic acid (20.00 g) in dichloromethane (400 ml) was stirred at room temperature under nitrogen for 2 hours and then added to a solution of pyridine (3.60 g) and 2,2-dimethyl-1,3-dioxane-4,6-dione (6.50 g) in dichloromethane over 5 minutes. The mixture was stirred at room temperature for 2 days, washed with ice-cold 2.5M hydrochloric acid and saturated brine, dried over $MgSO_4$ and evaporated. The residue was dissolved in water (300 ml) and acetic acid (150 ml) and refluxed for 5 hours. The mixture was evaporated and partitioned between diethyl ether (800 ml) and 10% aqueous sodium carbonate. The ether solution was dried over $MgSO_4$ and evaporated. The residue was chromatographed on silica (50 g) using 30% hexane in dichloromethane. Fractions which contained the pure product were evaporated to give the title compound (6.5 g), m.p. 117°–119°.

Analysis %: Found: C,55.41; H,5.17; N,3.46. $C_{21}H_{23}Cl_2NO_6$ requires: C,55.27; H,5.08; N,3.07.

(B)

1-{[4-(2,3-Dichlorophenyl)-3-ethoxycarbonyl-5-methoxycarbonyl-6-methyl-1,4-dihydropyrid-2-yl]methoxy}propan-2-ol A solution of 1-{[4-(2,3-dichlorophenyl)-3-ethoxycarbonyl-5-methoxycarbonyl-6-methyl-1,4-dihydropyrid-2-yl]methoxy}acetone (0.46 g) and sodium borohydride (0.10 g) in ethanol (40 ml) was stirred at room temperature for 5 hours. The solution was evaporated and the residue was dissolved in ethyl acetate and washed three times with water. The organic layer was dried over $MgSO_4$ and evaporated. The residue was crystallised from diethyl ether/hexane to give the title compound (0.20 g), m.p. 110°–113°.

Analysis %: Found: C,55.01; H,5.36; N,3.09. $C_{21}H_{25}Cl_2NO_6$ requires: C,55.03; H,5.50; N,3.06.

PREPARATION 5

4-Chloro-6-(1-methyl-2-imidazolylmethoxy)pyrimidine

Sodium hydride (0.30 g as an 80% dispersion by weight in oil) was added to a solution of 1-methyl-2-hydroxymethylimidazole (1.12 g) in tetrahydrofuran (30 ml) and the mixture stirred at room temperature for one hour. A solution of 4,6-dichloropyrimidine (1.48 g) in tetrahydrofuran (10 ml) was added to the reaction mixture dropwise over 30 minutes and the mixture stirred at room temperature for 3 hours and evaporated. The residue was taken up in dichloromethane and the solution extracted into 2M hydrochloric acid. The acidic layer was washed with dichloromethane, basified with saturated aqueous sodium hydrogen carbonate solution and extracted into dichloromethane. The organic layer was dried over $Na_2SO_4$ and evaporated to give the title compound (1.2 g), m.p. 126°–128° C. This compound was used directly in subsequent reactions.

PREPARATION 6

4-Chloro-6-(2-pyridylmethoxy)pyrimidine was prepared by the method described in Preparation 4 using 2-hydroxymethylpyridine, sodium hydride and 4,6-dichloropyrimidine as the starting materials. The product was obtained as an oil which was used directly in subsequent reactions.

We claim:

1. A dihydropyridine compound of the formula

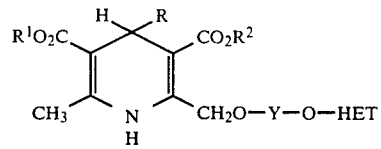

and a pharmaceutically acceptable acid addition salt thereof, wherein R is selected from the group consisting of 2-chlorophenyl and 2,3-dichlorophenyl; $R^1$ and $R^2$ are each alkyl having from one to three carbon atoms; Y is selected from the group consisting of —$(CH_2)_2$— and —$CH_2CH(CH_3)$—; and HET is selected from the group consisting of 2- and 4-pyrimidyl and substituted 2- and 4-pyrimidyl wherein said substituent is selected from the group consisting of carbamoyl, amino, alkoxy having from one to three carbon atoms, chloro, 2-aminoethylamino, 2-hydroxyethylamino, 2-pyridylmethylamino, 2,3-dihydroxypropylamino, 2-pyridylmethoxy, 1-methyl-2-imidazolylmethoxy and morpholino.

2. A compound of claim 1, wherein $R^1$ is methyl, $R^2$ is ethyl and Y is —$(CH_2)_2$—.

3. The compound of claim 2, wherein HET is 2-pyrimidyl and R is 2-chlorophenyl.

4. The compound of claim 2, wherein HET is 4-pyrimidyl and R is 2-chlorophenyl.

5. The compound of claim 2, wherein HET is 2-pyrimidyl and R is 2,3-dichlorophenyl.

6. The compound of claim 2, wherein HET is 4-pyrimidyl and R is 2,3-dichlorophenyl.

7. A compound of claim 2, wherein HET is substituted 4-pyrimidyl wherein said substituent is selected from the group consisting of carbamoyl, amino, alkoxy having from one to three carbon atoms, chloro, 2-aminoethylamino, 2-hydroxyethylamino, 2-pyridylmethylamino, 2,3-dihydroxypropylamino, 2-pyridylmethoxy, 1-methyl-2-imidazolylmethoxy and morpholino.

8. A compound of claim 7, wherein R is 2,3-dichlorophenyl.

9. A compound of claim 7, wherein R is 2-chlorophenyl.

10. A pharmaceutical composition comprising an anti-hypertensive or anti-ischaemic effective amount of a compound according to claim 1, together with a pharmaceutically acceptable carrier or diluent.

11. A method for treating hypertension in a mammal which comprises administering to said mammal an effective antihypertensive amount of a compound according to claim 1.

* * * * *